United States Patent
Franz et al.

(10) Patent No.: US 11,172,848 B2
(45) Date of Patent: Nov. 16, 2021

(54) SYSTEM AND PROCESS FOR MONITORING A POSITION STABILITY

(71) Applicant: Drägerwerk AG & Co. KGaA, Lübeck (DE)

(72) Inventors: Frank Franz, Lübeck (DE); Stefan Schlichting, Lübeck (DE); Jasper Diesel, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 0 days.

(21) Appl. No.: 17/014,470

(22) Filed: Sep. 8, 2020

(65) Prior Publication Data
US 2021/0068710 A1  Mar. 11, 2021

(30) Foreign Application Priority Data
Sep. 9, 2019  (DE) ...................... 10 2019 006 326.0

(51) Int. Cl.
*A61B 5/11* (2006.01)
*A61B 5/00* (2006.01)

(52) U.S. Cl.
CPC ............ *A61B 5/1115* (2013.01); *A61B 5/002* (2013.01); *A61B 5/0017* (2013.01); *A61B 5/1128* (2013.01); *A61B 5/746* (2013.01)

(58) Field of Classification Search
CPC ....................................................... H04N 7/18
See application file for complete search history.

(56) References Cited

U.S. PATENT DOCUMENTS

| | | |
|---|---|---|
| 2012/0075464 A1 | 3/2012 | Derenne et al. |
| 2014/0267625 A1 | 9/2014 | Clark et al. |
| 2019/0012893 A1 | 1/2019 | Johnson et al. |

FOREIGN PATENT DOCUMENTS

| | | |
|---|---|---|
| DE | 102009022555 A1 | 12/2010 |
| JP | 2013149156 A | 8/2013 |
| JP | 2014140447 A | 8/2014 |

(Continued)

OTHER PUBLICATIONS

English translation of JP2014140447A, Harukaze KK (Year: 2014).*
(Continued)

*Primary Examiner* — Brian A Zimmerman
*Assistant Examiner* — Cal J Eustaquio
(74) *Attorney, Agent, or Firm* — McGlew and Tuttle, P.C.

(57) ABSTRACT

A system (100) monitors a position stability of a person (105) located on a patient positioning device (104) within a medical setting monitored area (108) and includes a sensor unit (110) with optical sensors (112) real time outputting a sensor signal (114) sensor data indicating a sequence of three-dimensional views of the monitored area over a monitoring time. A processor unit (120) receives the sensor signal and determines, based on indicated three-dimensional views, a person's center of weight (121), a geometric reference value (123), and a geometric distance (D) between the center of weight and the geometric reference value and automatedly monitors the determined geometric distance in real time over a monitoring time and calculates a current position stability (127) as a function of the currently determined geometric distance and geometric distances determined within a past analysis time interval and outputs a position stability signal (129).

18 Claims, 6 Drawing Sheets

(56) References Cited

FOREIGN PATENT DOCUMENTS

| | | |
|---|---|---|
| JP | 2015132963 A | 7/2015 |
| JP | 2018126423 A | 8/2018 |
| JP | 2018143338 A | 9/2018 |
| WO | 2018037026 A1 | 3/2018 |

OTHER PUBLICATIONS

English translation of JP2018143338A, Omron Tateisi Electronics Co (Year: 2018).*
English translation of JP2015132963A, Chino Gijutsu KK (Year: 2015).*
English translation of JP2013149156A, Fujitsu LTD (Year: 2013).*
English translation, JP2018126423A, Minebeamitsumi Inc. (Year: 2018).*

* cited by examiner

SYSTEM AND PROCESS FOR MONITORING A POSITION STABILITY

CROSS REFERENCE TO RELATED APPLICATIONS

This application claims the benefit of priority under 35 U.S.C. § 119 of German Application 10 2019 006 326.0, filed Sep. 9, 2019, the entire contents of which are incorporated herein by reference.

TECHNICAL FIELD

The present invention pertains to a system and to a process for monitoring the position stability of a person located on a bed within a monitored area in a medical setting. The present invention further pertains to a program with a program code for carrying out the process according to the present invention.

TECHNICAL BACKGROUND

It is a known problem in a medical setting that patients, especially when they are confused, put their own treatment at risk by letting themselves fall out of their bed or moving on their bed in a position, in which there is an acute risk that they will fall out of bed. In order to prevent such an activity of the patient in his own interest in due time, it is known to provide a camera-based monitoring system for monitoring beds within a hospital.

Document US 2014/0267625 A1 describes a patient monitoring system, in which at least one plane is defined corresponding to the position of a bed. If a detected patient passes through this plane, an alarm is outputted, which indicates a hazardous current position of the patient on the bed.

SUMMARY

An object of the present invention is to make possible an improved automated monitoring of the position stability of a person located on a patient positioning device in a medical setting, especially an improved avoidance of the outputting of nuisance alarms and especially an early detection of relevant risks to the position stability.

A system for monitoring the position stability of a person located on a patient positioning device, especially on a bed, within a monitored area in a medical setting, with a sensor unit and with a processor unit, is proposed according to the present invention for accomplishing this object.

The sensor unit with a number of optical sensors is configured to determine a sensor signal and to output the sensor signal in real time. In this case, the number of optical sensors can, moreover, be arranged in a medical setting and are configured such that the sensor signal comprises sensor data, which indicate a sequence of three-dimensional views of the monitored area over a monitoring time.

The processor unit is configured to receive the sensor signal and to determine, on the basis of the indicated three-dimensional views, at least one person's center of weight, which comprises information about the person located on the patient positioning device within the monitored area. The processor unit is further configured to determine, on the basis of the indicated three-dimensional views, at least one geometric reference value that comprises information about the patient positioning device located within the monitored area. The processor unit is further configured to determine a geometric distance between the person's center of weight and the geometric reference value. Finally, the processor unit is further configured to automatedly monitor the determined geometric distance in real time (in an automated manner) over the course of a monitoring time and to calculate a current position stability value as a function of the currently determined geometric distance and as a function of geometric distances determined within a past analysis time interval and to output a corresponding position stability signal.

Within the framework of the present invention, it was found that a nuisance alarm can be avoided in an especially reliable manner when, in addition to currently determined values, such as the currently determined geometric distance in the present case, past geometric distances are also taken into consideration in the calculation of the current position stability value. Thus, a movement of the person's center of weight and/or the geometric reference value can be taken into consideration, which leads to an especially reliable current position stability value.

The system according to the present invention advantageously makes possible an automated monitoring of the position stability of the person located on the patient positioning device. By monitoring the geometric distance in real time, it is possible to rapidly respond to a change in the position of the person on the patient positioning device, for example, by outputting an alarm signal and/or by sending an alarm to another person, for example, to a medical staff member. In particular, the position stability signal is outputted independently of reaching possible threshold values, so that a more accurate checking of the situation in the monitored area can be triggered already in case of an unexpected reduction of the position stability.

It is especially advantageously possible to determine a currently present stasis of the person on the patient positioning device by monitoring the at least one person's center of weight.

The patient positioning device is preferably a bed or a chair or the like.

The at least one person's center of weight is in this case a geometric point in space, which indicates information about a weight located on the patient positioning device, especially about a distribution of the weight of the person located on the patient positioning device. In this connection, in addition to the weight of the person, the weight of a bedspread located on the patient positioning device or of other objects located on the patient positioning device may also be taken into consideration. A total weight located on the patient positioning device as well as the position thereof may especially be estimated on the basis of the sensor signal, and the person's center of weight can be determined on the basis of this estimation.

The person located on the patient positioning device is typically a patient on a hospital bed within a hospital. However, the patient may also be a person requiring care within a care facility or the like.

The detection of a person's center of weight and a geometric reference value advantageously makes it possible to further process very few data, so that as a result a monitoring in real time is especially advantageously possible.

The position stability signal indicates the calculated current position stability value. In this case, the position stability signal can be outputted directly via an output unit or be further processed via an additional unit in order to obtain a current output and/or an output accumulated over earlier times, especially a graphic output, of the position stability value.

The automated monitoring typically takes place in time increments, wherein the at least one person's center of weight and the at least one geometric reference value, as well as its geometric distance are determined for each time increment. The monitoring is automated in the sense that no manual input has to be carried out by a user of the system for a concrete time increment of the monitoring.

That the monitoring takes place in real time means especially that the current position stability value is calculated within a monitoring time increment or is at least largely calculated. Monitoring time increments are in this case, for example, time increments of at least 0.1 sec, especially of at least 0.5 sec, e.g., of 1.0 sec.

The sensor data that make it possible to determine a three-dimensional view of the monitored area can according to the present invention be data indicating a two-dimensional arrangement. The sequence of three-dimensional views according to the present invention is obtained from a temporal sequence of individual sensor data related to the sensor signal outputted in real time. According to the present invention, three-dimensional views may also be three-dimensional point clouds. These three-dimensional point clouds make possible a highly reduced storage and transmission cost compared to the transmission of full images. In particular, the three-dimensional point cloud may be reduced to relevant parts of the monitored area by an automated prefiltering, for example, on the basis of detected brightness contrasts, so that large single-color surfaces, for example, a floor, can be removed from the determined sensor data.

The detailed configuration of a sensor unit according to the present invention with a number of optical sensors for providing a sequence of three-dimensional views is known and such sensor units are already commercially available, so that a detailed explanation of the manner of operation of this sensor unit is dispensed with below.

Preferred embodiments of the system according to the present invention will be described below.

The calculation of the position stability value preferably comprises calculation of a function value for a current geometric distance and a taking into account, especially adding up, of earlier function values recorded within the analysis time interval with the currently calculated function value. For example, a function value averaged over the analysis time interval can in this case be determined over time as a position stability value. Such a calculation rule may be carried out iteratively in an especially simple and rapid manner.

In one advantageous embodiment, the system has, furthermore, an alarm generation unit, which is configured to receive the position stability signal and to output an alarm generation signal in case a currently calculated position stability value reaches a predefined threshold value. Advantageously, it is ensured in this embodiment that a corresponding alarm indicated by the alarm generation signal is outputted in case of a very high risk that the person located on the patient positioning device could fall out of the patient positioning device, i.e., in the presence of a very low position stability. The alarm generation signal can in this case trigger a visual and/or acoustic alarm. In an alternative embodiment, the system according to the present invention is configured to trigger an alarm generation signal of an external alarm generation unit by the position stability signal. In different variants of this embodiment, the reaching of the predefined threshold value may mean that the currently calculated position stability value has dropped to the predefined threshold value, or that the currently calculated position stability value has increased to the predefined threshold value.

Medical staff is preferably informed about the existence of a low position stability by an outputted alarm generation signal. In another additional or alternative embodiment, the alarm generation unit is arranged such that an alarm, which informs him about the risk of an unstable position, is optically or acoustically outputted to the person located on the patient positioning device. Consequently, the person is advantageously given the possibility of changing his position himself such that there is no more risk to his position stability.

The person's center of weight is at least partly determined based on a predefined body weight model and on person-specific personal data determined from the indicated three-dimensional view in an especially advantageous embodiment. The determined person-specific personal data comprise a probable position of the extremities of the person located on the patient positioning device. In a variant of this exemplary embodiment, the predefined body weight model comprises an estimate of the distribution of the weight of the person on the basis of his height and/or of other geometric body measurements, especially on the basis of a measured hip circumference, of a measured leg length and/or of a measured arm length.

In another especially advantageous embodiment, the person's center of weight is at least partially determined based on a detection of moving regions on the patient position device, which regions are indicated by the temporal sequence of three-dimensional views. Moving regions on the patient positioning device typically belong to the person located on the patient positioning device or are, for example, in case of a bedspread, arranged in the immediate vicinity of this person and hence move because of a movement of the person. Therefore, the person's center of weight, which corresponds approximately to an actual center of the person located on the patient positioning device, can in this embodiment advantageously be determined by an especially simple image processing process. The algorithms for the detection of active points in a sequence of three-dimensional views are known and are therefore not explained in detail below.

In another advantageous embodiment, the processor unit is further configured to determine, on the basis of the indicated three-dimensional views, a plurality of centers of weight of a person and to determine thereby a position pattern of the person located on the patient positioning device. The determined plurality of centers of weight of a person preferably indicate an arrangement of the extremities and/or of the trunk of the person on the patient positioning device. In an especially preferred variant of this embodiment, the determination of the plurality of centers of weight of the person is based on a predefined body weight model and/or on person-specific personal data determined from the indicated three-dimensional view. In another variant of this embodiment, a corresponding weighting factor is associated with each person's center of weight from the plurality of centers of weight of the person. In this variant, a total center of weight, which indicates an actual center of the person, is preferably formed based on the correspondingly weighted centers of weight of the person. The corresponding weighting factors are typically dependent on the predefined body weight model and/or on the determined person-specific personal data.

In another especially preferred embodiment, the determined geometric reference value comprises at least one plane characterizing the patient positioning device. The plane characterizing the patient positioning device is preferably a plane at right angles to the support surface of the patient positioning device, which comprises an edge, especially a bed edge. In a preferred variant of this embodiment, at least three geometric reference values, especially four geometric reference values are determined, wherein each of these geometric reference values is a plane characterizing the patient positioning device, and wherein each of these planes comprises a respective edge of the patient positioning device, especially a respective edge of the bed and is aligned at right angles to the support surface of the patient positioning device. In this embodiment, it is advantageously possible to determine a distance between the person's center of weight and the characterizing plane in order to calculate the position stability value on the basis of the change of this distance over the course of the past analysis time interval. In an advantageous example of the variant with a plurality of characterizing planes, the position stability value is only determined on the basis of the geometric distance that is the shortest. As a result, only the geometric reference value that is most critical for the position stability is taken into consideration in the calculation of the patient stability value. In another variant of this embodiment, the plane characterizing the patient positioning device is a bed surface and the patient positioning device is a bed. In this variant, a distance of the person's center of weight from the bed surface can advantageously be taken into consideration for the calculation of the patient stability value, as a result of which, for example, standing of the person on the bed is detected as an unsecure position of the person.

The analysis time interval is at least 1 sec, preferably at least 5 sec, especially at least 10 sec. In this embodiment, the analysis interval is advantageously predetermined such that the development of a movement of the person's center of weight relative to the geometric reference value can be analyzed in a reliable manner. It is thus avoided, particular, that the current position stability value indicates a risk even though a movement of the person's center of weight into the direction of a secure position has already begun.

In a preferred embodiment, a geometric distance decreasing within the monitoring time indicates a decrease of a position stability of the person located on the patient positioning device. The system according to the present invention in a preferred embodiment outputs in any case a position stability signal, which indicates an alarm generation, if the geometric distance is zero or almost zero.

In another embodiment, the calculated position stability value is, furthermore, dependent on an activity index determined by the processor unit, wherein the activity index is based on an analysis of past three-dimensional views for the person currently located on the patient positioning device. An inactive person, i.e., a person with a low activity index, cannot put his position stability at risk, whereas there is a basically higher risk for an especially active person that he will put himself into a hazardous position. In this embodiment, a change of the person's center of weight relative to the geometric reference value can therefore be analyzed over time weighted with the activity index. In a variant of this embodiment, the activity index indicates an activity of a body part of the patient, such as of the head or arm, wherein the activity of this body part represents an activity indicator of the entire body of the patient.

In another embodiment, the calculated position stability value is, furthermore, dependent on a position securing index determined by the processor unit, wherein the position securing index is based on a detection of at least one position securing object in the three-dimensional views from a predefined group of position securing objects. In an especially advantageous variant of this embodiment, the patient positioning device is a bed and the predefined group of position securing objects comprises a bed rail. The presence of an upraised or lowered bed rail has a considerable share in the risk that a person will fall out of bed. It is thus especially advantageously avoided in this embodiment that a high risk for the position stability is detected even though bed rails, which counteract a risk to the position stability, are present on the bed. Therefore, the outputting of a nuisance alarm is especially advantageously avoided and the reliability of the patient stability signal is supported.

In another embodiment, the calculated position stability value is, furthermore, dependent on a rate of distance change determined by the processor unit, wherein the rate of distance change is based on a change of the determined geometric distances. In this embodiment, it is advantageously taken into consideration whether the person's center of weight relative to the geometric reference value moves rapidly or slowly. In principle, a higher risk to the person assumes a rapid movement, whereas a slow movement can typically lead only slowly to a risk to the position stability. Furthermore, in this embodiment, a directed movement can advantageously be detected, which may especially lead rapidly to a risk to the current position of the person on the patient positioning device. Preferably in this embodiment, in addition to the rate of distance change, the direction of distance change is also detected. In another variant, the kinetic energy of the weight points moving on the patient positioning device and/or or the person located on the patient positioning device is determined by the estimated weight and the determined rate of distance change. In another variant, in addition to the rate of distance change, a change in direction is also detected, and as a result, a rotation of the person located on the patient positioning device is inferred.

In another embodiment, the calculated position stability value is, furthermore, based on a detection of the extremities of the person by the processor unit and on a current position of the extremities in relation to the person's center of weight and/or to the geometric reference value. In a variant of this embodiment, it is detected by the system whether a person is pulling or is pressing on a part of the patient positioning device and as a result, a risk to his position stability may arise.

In another embodiment, the calculated position stability value is, moreover, based on a detection by the processor unit of at least one hazardous event in the three-dimensional views from a predefined group of hazardous events. In this embodiment, the predefined group of hazardous events preferably comprises predefined movement patterns, which have in the past led to a risk to the position stability of the person or of another person. For example, in a variant of this embodiment, a hazardous event is an incipient rolling movement of the person. In another variant, a hazardous event is a bowing of the head of the person over a bed rail of the patient positioning device, which is configured as a bed.

In an embodiment according to the present invention, the system is activated and/or deactivated via a manual user input via a user interface, for example, a touch display, a keyboard, an adjusting knob or a joystick. In an additional or alternative embodiment, the monitoring process is activated by the system in an automated manner by a detection by the processor unit of the upraising of a bed rail of the patient positioning device, which is configured as a bed, on the basis of the indicated three-dimensional views. In an additional variant of this embodiment, the deactivation of the monitoring process is carried out by a corresponding detection by the processor unit of the lowering and/or the removal of the bed rail.

According to another aspect of the present invention, a process for monitoring the position stability of a person located on a patient positioning device, especially on a bed, within a monitored area in a medical setting is proposed for accomplishing the above-mentioned object. The process according to the present invention has the steps indicated below:
- determination and outputting of a sensor signal in real time, wherein the sensor signal comprises sensor data, which indicate a sequence of three-dimensional views of the monitored area over a monitoring time,
- reception of the sensor signal,
- determination of at least one person's center of weight on the basis of the indicated three-dimensional views, wherein the at least one person's center of weight comprises information about the person located on the patient positioning device within the monitored area,
- determination of a geometric reference value on the basis of the indicated three-dimensional views, wherein the geometric reference value comprises information about the patient positioning device located within the monitored area,
- determination of a geometric distance between the person's center of weight and the geometric reference value,
- automated monitoring of the determined geometric distance in the course of a monitoring time in real time,
- calculation of a current position stability value as a function of the currently determined geometric distance and geometric distances determined within a past analysis time interval, and
- outputting of a corresponding position stability signal.

The process according to the present invention especially advantageously makes possible a reliable estimation of the current position stability by taking past geometric distances into consideration. As a result, a change of the person's center of weight relative to the geometric reference value can be analyzed for the assessment of the current position stability. Consequently, nuisance alarms can be avoided, and an especially reliable position stability value can be calculated.

Furthermore, the process according to the present invention makes it possible to especially rapidly calculate the current position stability value by carrying out a few calculation steps.

A detailed explanation on different variants of the calculation of the position stability value will be described within the framework of the description of the figures.

In principle, the different process steps are carried out in the sequence shown, and the at least one person's center of weight and the at least one geometric reference value may also be determined in the reverse sequence. Furthermore, the first process steps are already carried out for a new monitoring time, while the final process steps are also carried out for the previous monitoring time.

The first two process steps concerning the sensor signal are typically carried out repeatedly in real time, i.e., in short consecutive time increments. Short consecutive time increments are in this case, for example, time increments of at least 0.1 sec, especially of at least 0.5 sec, e.g., time increments of 1.0 sec.

In an embodiment of the process according to the present invention, this process is stopped in case a medical staff member is detected by the processor unit within the monitored area. Such a detection can take place, for example, by reading an identification number carried along by the medical staff member. The process according to this embodiment is preferably continued together with the previously determined position stability values, as soon as the medical staff member has left the monitored area again. In an alternative embodiment, this process is stopped only if a medical staff member is detected by the processor unit within the monitored area and the person and/or the patient positioning device is additionally located in the detected field of view of the medical staff member.

Furthermore, a program with a program code for carrying out the process according to the present invention is proposed for accomplishing the above-mentioned object when the program code is run on a computer, on a processor or on a programmable hardware component.

The program can in this case also execute only a part of the data processing according to the present invention. At least the functions of the processor unit are preferably controlled by a program and/or by parts of the program that are coordinated with one another. In particular, the processing of the sensor data related to the sensor signal is controlled by a separate part of the program within a processor of the sensor unit in embodiments of the program according to the present invention. The program according to the present invention is preferably run on a processor of the system according to the present invention. As an alternative, the program is run at least by a first processor of the processor unit and by a second processor of the sensor unit.

The present invention shall now be explained in more detail on the basis of advantageous exemplary embodiments, which are schematically shown in the figures.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
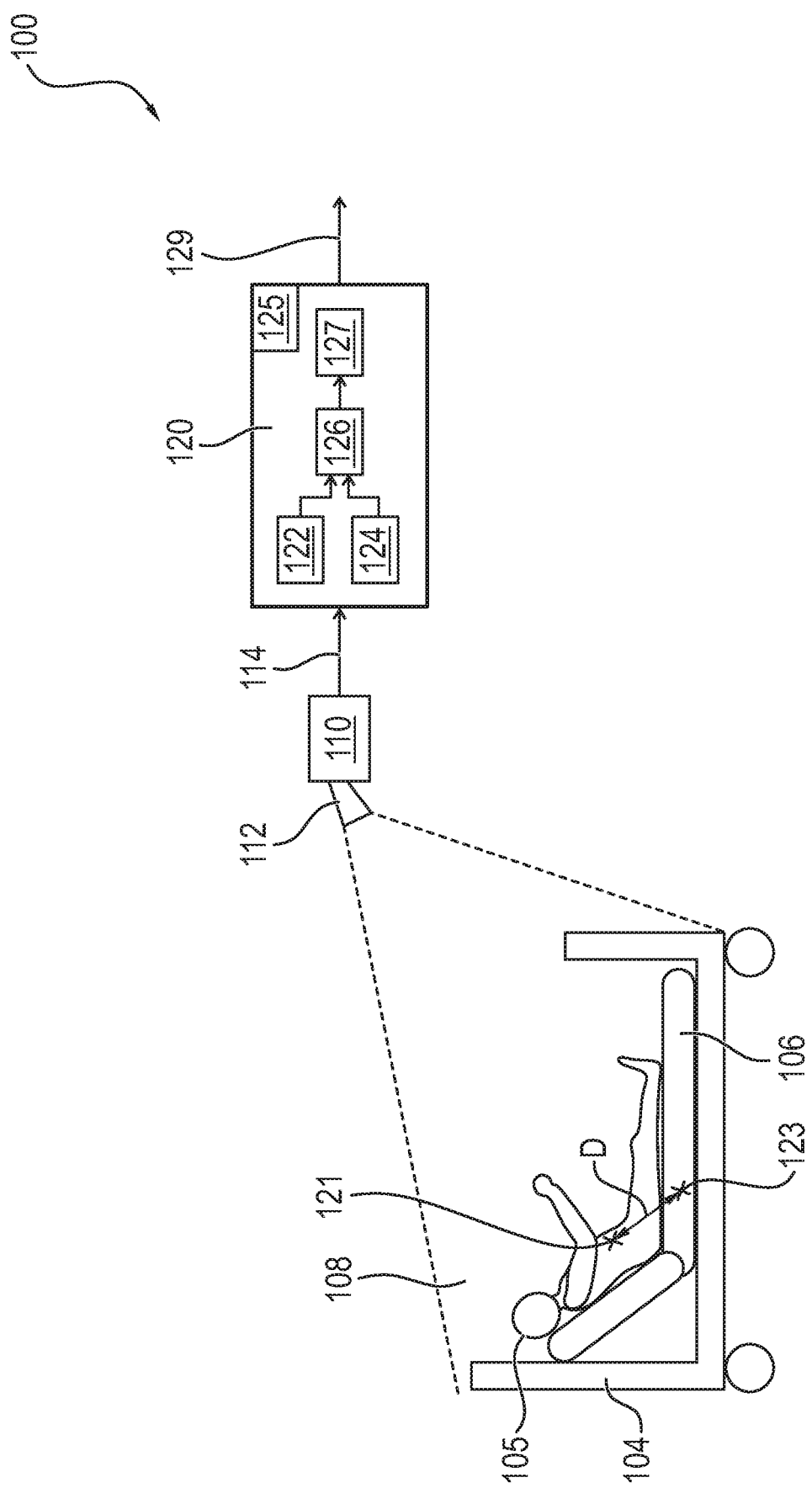
FIG. 1 is a schematic view of a first exemplary embodiment of the system according to the present invention.

Referring to the drawings, FIG. 1 shows a schematic view of a first exemplary embodiment of the system 100 according to the present invention.

The system 100 for monitoring a position stability of a person 105 located on a patient positioning device 104, on the bed 104 in the present case, within a monitored area 108 in a medical setting, comprises a sensor unit 110 and a processor unit 120.

The sensor unit 110 has a number of optical sensors 112 and is configured to determine a sensor signal 114 and to output it in real time. In this connection, the number of optical sensors 112 can, moreover, be arranged in a medical setting and are configured such that the sensor signal 114 comprises sensor data, which indicate a sequence of three-dimensional views of the monitored area 108 during a monitoring time. In the exemplary embodiment shown, the number of optical sensors 112 is installed within a housing, wherein a three-dimensional view of the monitored area 108 is indicated by the sensor data due to the different position of the optical sensors 112.

In the exemplary embodiment being shown, the sensor signal 114 is outputted to the processor unit 120 in a wireless manner via a wireless connection, for example, via WLAN, Bluetooth, BLE or ZigBee. In an exemplary embodiment, not shown, the output of the sensor signal is carried out in a cable-based manner, for example, within the framework of a bus system, especially of an Ethernet system.

The processor unit 120 is configured to receive the sensor signal 114. The processor unit 120 is further configured to determine, on the basis of the indicated three-dimensional views, in a first processing step 122 at least one person's center of weight 121, which comprises information about the person 105 located on the bed 104 within the monitored area 108. The person's center of weight in the exemplary embodiment shown is located outside of the body of the person 105 because of the curved stature of the person. The person's center of weight is in the present case a real center of the person 105 at least partially estimated based on a predefined body weight model and on person-specific personal data determined from the indicated three-dimensional view. All objects located on the bed are in the exemplary embodiment shown taken into consideration for the determination of the person's center of weight 121. Since there is no bedspread on the person 105 in the present case, the person's center of weight corresponds approximately to the actual center of the person 105.

The processor unit 120 is further configured to determine in a second processing step 124, on the basis of the indicated three-dimensional views, at least one geometric reference value 123 which comprises information about the bed 104 located within the monitored area 108. In the exemplary embodiment shown, the geometric reference value 123 is an actual center of the bed mattress 106 of the bed 104. The actual center is in the present exemplary embodiment at a predetermined position, which is stored in the processor unit corresponding to its alignment in relation to the bed frame of the bed 104. A storage modulus 125 is preferably provided for this purpose within the processor unit 120. In an exemplary embodiment, not shown, the center of the bed mattress is estimated by the processor unit on the basis of a predefined mattress weight model.

The processor unit 120 is further configured to determine a geometric distance D between the at least one person's center of weight 121 and the at least one geometric reference value 123 in another processing step 126 on the basis of the least one geometric reference value 123 and of the at least one person's center of weight 121. The geometric distance D is in the present case an actual direct distance between these two points within at least one three-dimensional view from the sensor signal 114.

Finally, the processor unit 120 is further configured to monitor the determined geometric distance D in real time in an automated manner over the course of a monitoring time and to calculate a current position stability value 127 as a function of the currently determined geometric distance D and of geometric distances determined within a past analysis time interval and to output a corresponding position stability signal 129. In the exemplary embodiment being shown, the currently determined geometric distance D is stored in the storage modulus 125, so that this earlier measured geometric distance can be accessed in future time increments for calculation of the current position stability value 127. In an exemplary embodiment, not shown, stored data are stored in an external network, which can be accessed by the processor unit.

A detailed description of the calculation of the position stability value 127 is found below within the framework of the description of FIGS. 3 and 4.

The position stability signal 129 is outputted in real time according to the present invention. As a result, a user of the system according to the present invention is able to detect at any time the risk of a reduction of the position stability. It is possible to especially rapidly estimate the position stability of a concrete person 105 due to the outputting of a concrete position stability value 127, so that a large group of people can already be monitored by a few staff members. The monitoring of image data prevents the risk that a certain time interval must be seen in order to estimate a current movement of the person 105, whereas the outputted position stability signal 129 already comprises all relevant information about the estimation of the position stability of a concrete person 105.

The position stability signal 129 may preferably indicate that a predefined threshold value was reached by the currently calculated position stability value 127, so that the position stability signal additionally comprises alarm generation information.

In the exemplary embodiment shown, the position stability signal 129 is outputted in a cable-based manner. In an exemplary embodiment, not shown, this outputting is carried out by a wireless connection, as it is known in the field of communication technology in different variants.

In this connection, the position stability signal 129 is in the present case outputted to an external monitoring device (not shown), which does not belong to the present invention.

In the exemplary embodiment shown, all units of the system 100 according to the present invention have separate housings, since all units are arranged at a spaced location from one another. It is, as a result, possible, for example, to provide the processor unit at a central location in the medical setting and to operate a number of systems according to the present invention with a corresponding number of different sensor units with a common processor unit.

In an exemplary embodiment, not shown, the patient positioning device is a chair, a daybed, a stool or the like.

Figure 2:
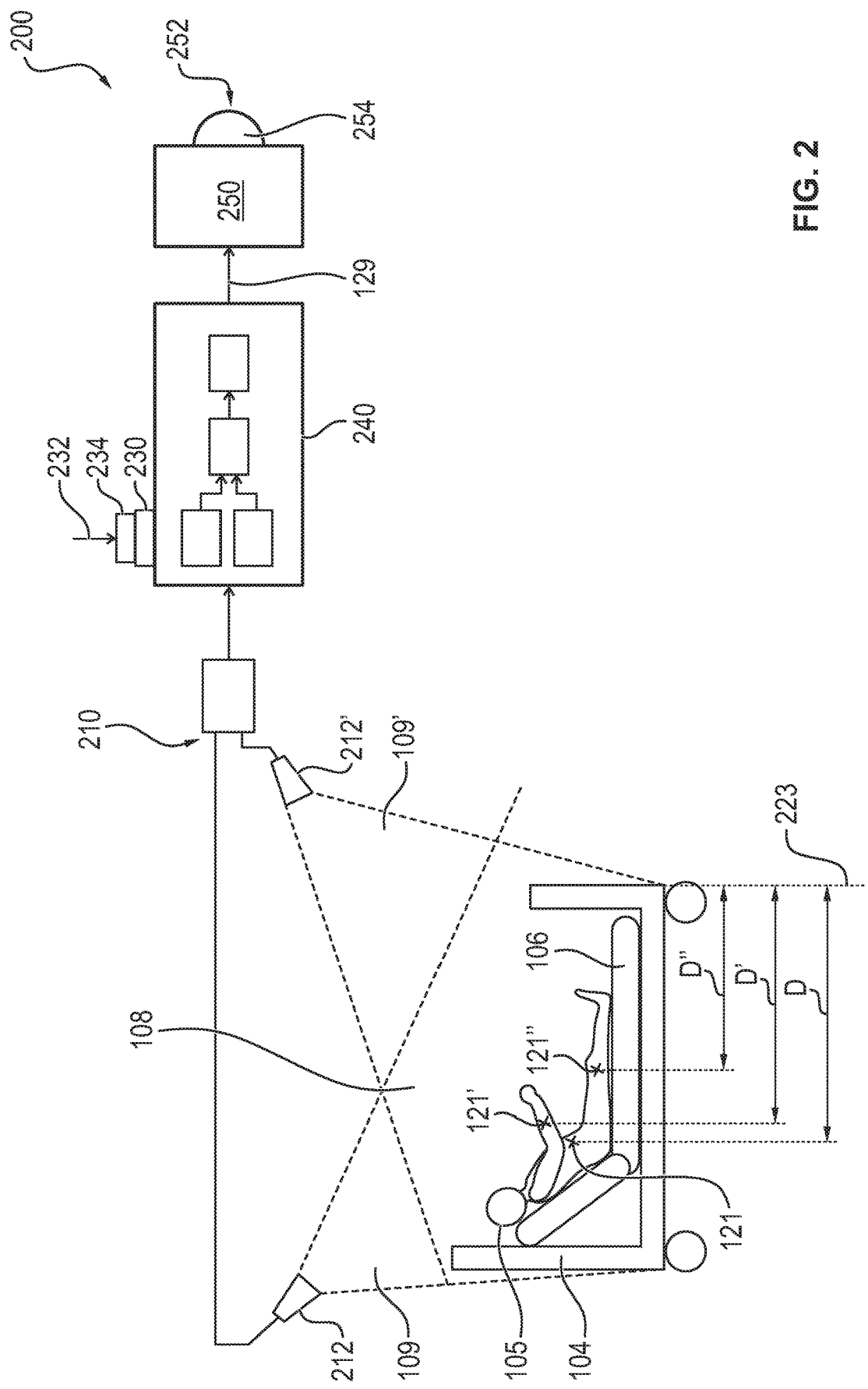
FIG. 2 is a schematic view of a second exemplary embodiment of the system according to the present invention.

FIG. 2 shows a schematic view of a second exemplary embodiment of the system 200 according to the present invention.

The system 200 differs from the system 100 shown in FIG. 1, among other things, by the sensor unit 210 comprising two separate cameras with a corresponding number of optical sensors 212, 212' and two partial monitored areas 109, 109'. A combined processing of the correspondingly detected sensor data is possible because the partial monitored areas 109, 109' have a common monitored area 108 to be monitored as an intersection over union. A single sequence of three-dimensional views of this common monitored area 108 to be monitored is consequently indicated.

The system 200 further differs from the system 100 from FIG. 1 by the processor unit 120 having a user interface 230 as an additional component of the system 200. The user interface 230 is arranged in a housing 240 of the processor unit 120 and is configured to receive a user input 232. In the present case, the user interface 230 has for this a touch display 234. In an alternative and/or additional exemplary embodiment, not shown, the user interface has a keyboard, an adjusting knob and/or a joystick. In the present case, the user input 232 indicates, for example, a switching on or a switching off of the processor unit 120. Furthermore, in the present case, person-specific personal data can be entered manually via the user interface 230 to determine the at least one person's center of weight 121 at least partially based thereon.

In the exemplary embodiment shown, the at least one person's center of weight 121 is a total of five centers of weight 121, 121', 121" of the person, of which three are shown, and which indicate a position pattern of the person 105 located on the bed 104. The plurality of centers of weight 121, 121', 121" of the person indicates here centers for the extremities and the trunk of the person located on the bed. The processor unit 120 is configured in the present case to determine the corresponding geometric distances D, D', D" to the geometric reference value 120 on the basis of the plurality of centers of weight 121, 121', 121" of the person. In an exemplary embodiment, not shown, the processor unit is configured to determine a current center of the person located on the bed on the basis of a plurality of centers of weight of the person and to determine the geometric distance to the geometric reference value on the basis of this center. A corresponding exemplary calculation of the position stability value is explained within the framework of the description of FIGS. 3 and 4.

In the present case, the geometric reference value 223 is at least one plane characterizing the bed 104. Only the plane on the foot side of the person 105 is shown here. The plane characterizing the bed 104 is configured at right angles to the bed mattress 106 and comprises at least one edge of the bed 104. In this case, a plane is at right angles to the bed mattress 106 when it is also at right angles to the floor under the bed 104, since changes in the mattress alignment, for example, for adjusting a sitting position of the person, typically do not change the geometric reference value.

The system 200 shown further comprises an alarm generation unit 250, which is configured to receive the position stability signal 129 and to output an alarm generation signal 252, if a currently calculated position stability value 127 reaches a predefined threshold value. The alarm generation signal 252 is in the present case an optical alarm generation signal, which is outputted via an illuminating device 254. The illuminating device 254 preferably does not illuminate as long as the predefined threshold value was not reached and illuminates in a characterizing shade of color, for example, a red shade, if the predefined threshold value is reached. In an exemplary embodiment, not shown, the alarm generation signal is an acoustic alarm generation signal. In the exemplary embodiment shown, the alarm generation unit 250 is a unit, which has a housing separate from the processor unit 120. As a result, the alarm generation unit 250 may advantageously be arranged at a location especially suitable for the alarm generation, e.g., at a location at which the medical staff stays.

Figure 3:
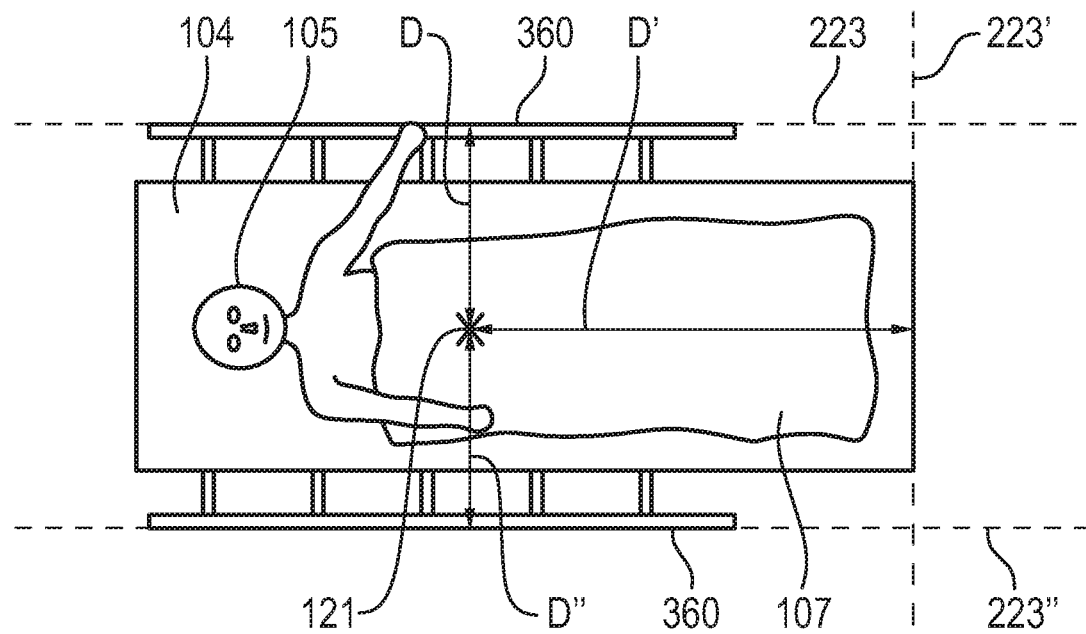
FIG. 3 is a schematic view of a third exemplary embodiment of the system according to the present invention, wherein an interaction with a position stability object is taken into consideration in the calculation of the current position stability value.
Figure 4:
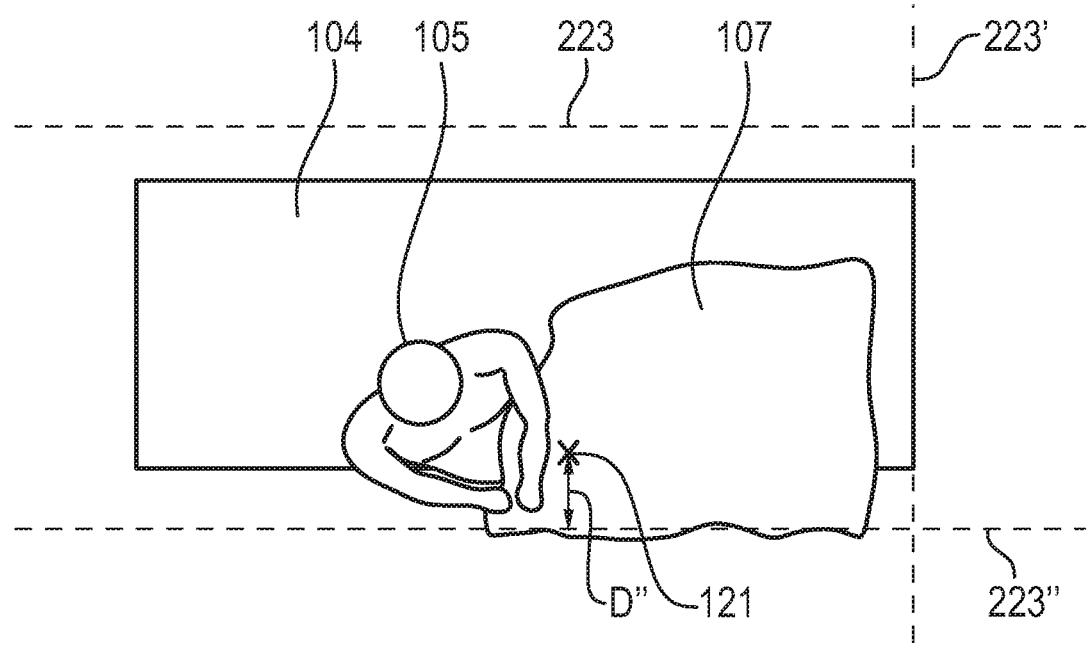
FIG. 4 is a schematic view of a third exemplary embodiment of the system according to the present invention, wherein a displacement of the person's center of weight in the direction of a geometric reference value is taken into consideration in the calculation of the current position stability value.

FIG. 3 and FIG. 4 show schematic views of a third exemplary embodiment of the system according to the present invention, wherein an interaction with a position securing object (FIG. 3) and a displacement of the person's center of weight in the direction of a geometric reference value (FIG. 4) are respectively taken into consideration in the calculation of the current position stability value. Within the framework of these two figures, only the position of the person 105 on the bed 104 is shown to explain the calculation of the position stability value against this background on the basis of the diagrams from FIGS. 5 and 6.

FIG. 3 shows the person 105 under a bedspread 107 while he grasps a position securing object 360, namely a bed rail mounted on the bed 104, with his hand.

The person's center of weight 121 is in the present case a point within the monitored area, which was determined by the processor unit by an estimation of a distribution of the weight located on the bed 104. For this, a weight can be associated with each point of a three-dimensional, detected set of points in order to determine the person's center of weight 121 on the basis of the weight distribution that developed as a result.

The at least one geometric reference value 223, 223', 223" is in the present case three planes, which are configured at right angles to the reclining surface of the bed 104 and comprise an edge of the bed 104. These are the three planes, which are formed by the two bed edges formed laterally to the person 105 and in the direction of the feet of the person 105. Correspondingly, three different geometric distances D, D', D" are present in the exemplary embodiment shown. At right angles to the reclining surface preferably also means at right angles to a floor under the bed 104.

The position stability value is calculated, in principle, such that a function $f(D(t_a))$ dependent on the geometric distance D is calculated for the currently determined geometric distance at the current time $t_a$ and is added with the function values of earlier times $t_{a-n}$ to the current position stability value $$L(t_a, T) = \frac{1}{T+1} \sum_{t_x = t_a - T}^{t_a} f(D(t_x)).$$

In this case, T describes the analysis interval to be analyzed for the calculation of the position stability value, and it is added over the different time increments within this analysis interval. The prefactor ensures an averaging of the calculated function values and is not used in other exemplary embodiments.

In the exemplary embodiment shown, the rule for the determination of the position stability value shown in the previous paragraph is adapted to the extent that because of the three different reference values 223, 223', 223", there are three different geometric distances D, D', D" to be analyzed, which can, for example, be taken into account as follows in the position stability value $L(t_a, T)$:

$$L(t_a, T) = \frac{1}{3(T+1)} \sum_{t_x=t_a-T}^{t_a} \sum_{d \in \{D,D',D''\}} f(d(t_x)).$$

A plurality of centers of weight of a person would lead to correspondingly more geometric distances to be taken into consideration. However, the fundamental calculation rules from the above paragraph can also be used for such exemplary embodiments. A weighting factor may additionally be used when taking into consideration a plurality of centers of weight of a person to take into consideration different weights associated with a person's center of weight in the calculation of the position stability value. In the exemplary embodiment being shown, the weight of the left arm of the person 105 could, for example, be detected as dangerously close to a lateral plane as a geometric reference value, while the weighting factors guarantee that a fundamentally secure position is detected in view of the predominant share of weight at a secure distance to the geometric reference value.

In the exemplary embodiment shown, the presence of the upraised bed rail as a position securing object 360 is preferably taken into consideration in the calculation of the position stability value. This can take place, for example, by a general adding up of a constant value $R(t_x)$ at the function $f(D(t_x))$, for each time $t_x$, at which the position securing object 360 was active:

$$L(t_a, T) = \frac{1}{T+1} \sum_{t_x=t_a-T}^{t_a} (f(D(t_x)) + R(t_x)).$$

The function $R(t_x)$ may be, for example, a step function, which assumes the value 1 if a position securing object 360 is present, and which assumes the value 0 in all other cases. In an exemplary embodiment, not shown, this function is dependent on whether the position securing object is located in the immediate vicinity of at least one determined person's center of weight.

In the exemplary embodiment being shown, the position stability value is preferably dependent on whether the person 105 is grasping the position securing object 360, i.e., the bed rail. In case of a detected grasping, the function $R(t_x)$ is reduced by a constant value, for example, 0.5. As a result, the fact that there is a certain risk that the person 105 will fall out of the bed 104 can be taken into consideration in the calculation of the position stability value. In this exemplary embodiment, at least the hands of the person 105 are detected by the processor unit. In another exemplary embodiment, all the extremities of the person are detected by the processor unit.

The situation shown in FIG. 4 differs from the situation shown in FIG. 3 to the extent that no position securing object is provided, and the person 105 is additionally oriented upright in the direction of a geometric reference value 223, 223', 223", namely of a lateral edge of the bed. In addition, the bedspread 107 has partially slid down from the bed 104 in the direction of the orientation of the person 105.

The determination of the at least one person's center of weight differs from the previous examples to the extent that this determination is at least partially based on a detection of moving regions on the bed 104. In particular, only the estimated weight of the moving regions above the bed 104 is taken into consideration for the determination of the person's center of weight. The movements of the bedspread 107 and of the person 105 were detected in this case, so that the person's center of weight has a very short geometric distance D" from the lateral geometric reference value 223".

In an exemplary embodiment, not shown, the distance from the different distances corresponding to the different geometric reference values is taken into account as the geometric distance that is the shortest. In this way, a geometric reference value that is especially relevant for the current position stability can be used for the calculation of the position stability value.

In the exemplary embodiment shown, an activity index $A(t_x)$ is preferably determined because of the detected movement for a respective time increment, which leads to a reduction of the position stability value in case of increasing activity of the person 105. In another exemplary embodiment, the activity index is only based on an estimate of the activity of the person, but not, as in the present exemplary embodiment, additionally on an activity of objects located on the bed, for example, of the bedspread 107. Within the framework of the exemplary calculation rule mentioned above, the activity index $A(t_x)$ can, for example, be taken into consideration as follows:

$$L(t_a, T) = \frac{1}{T+1} \sum_{t_x=t_a-T}^{t_a} (f(D(t_x)) + \partial(1 - A(t_x))).$$

In this case, $\partial$ is a weighting factor, which determines the influence of the activity index on the position stability value, and the activity index is a number between 0 and 1.

In an exemplary embodiment, not shown, the processor unit is further configured to determine the position stability value as a function of a rate of distance change. The rate of distance change is in this case determined by the processor unit due to a change of the determined geometric distances. For example, a detected movement can advantageously be detected by taking the rate of distance change into consideration. A directed movement, which takes place over a plurality of time increments, indicates the risk of a reduction in the position stability, for example, because a person is moving on the bed uniformly in the direction of an edge of the bed. In addition to the rate of distance change, a direction of distance change may advantageously also be determined, and the position stability value can be calculated based on it.

In another exemplary embodiment, not shown, the calculated position stability value is dependent on the detection of a hazardous event. Thus, a present hazardous event, for example, a rotation of the person out of bed, can be detected by the processor unit from a predefined group of hazardous events. This detection of hazardous events is, however, only an additional factor in the calculation of the position stability value according to the present invention.

Figure 5:
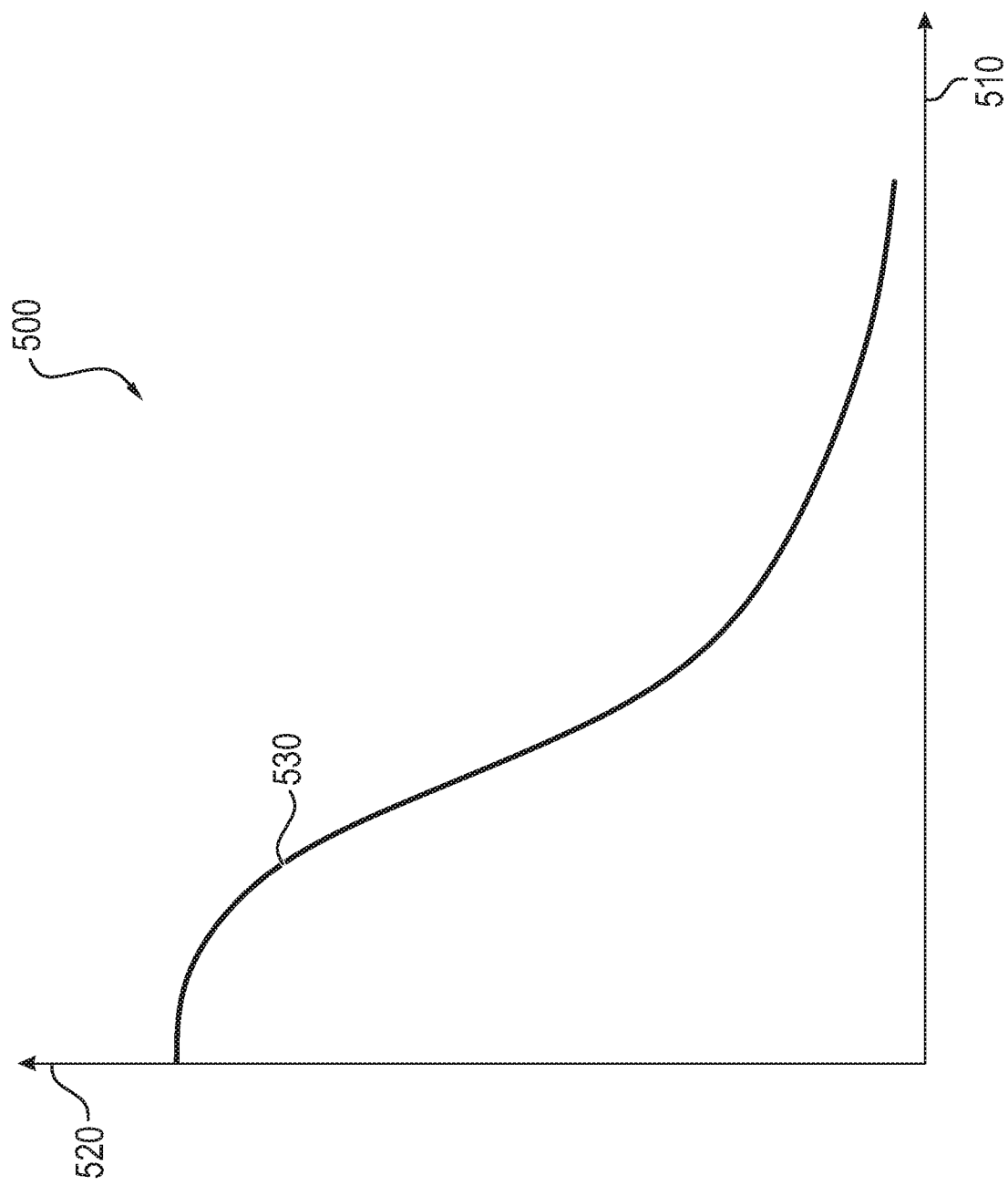
FIG. 5 is a diagram for the calculation of the current position stability value according to an exemplary embodiment of the system according to the present invention, wherein a geometric distance between two points is taken into consideration.
Figure 6:
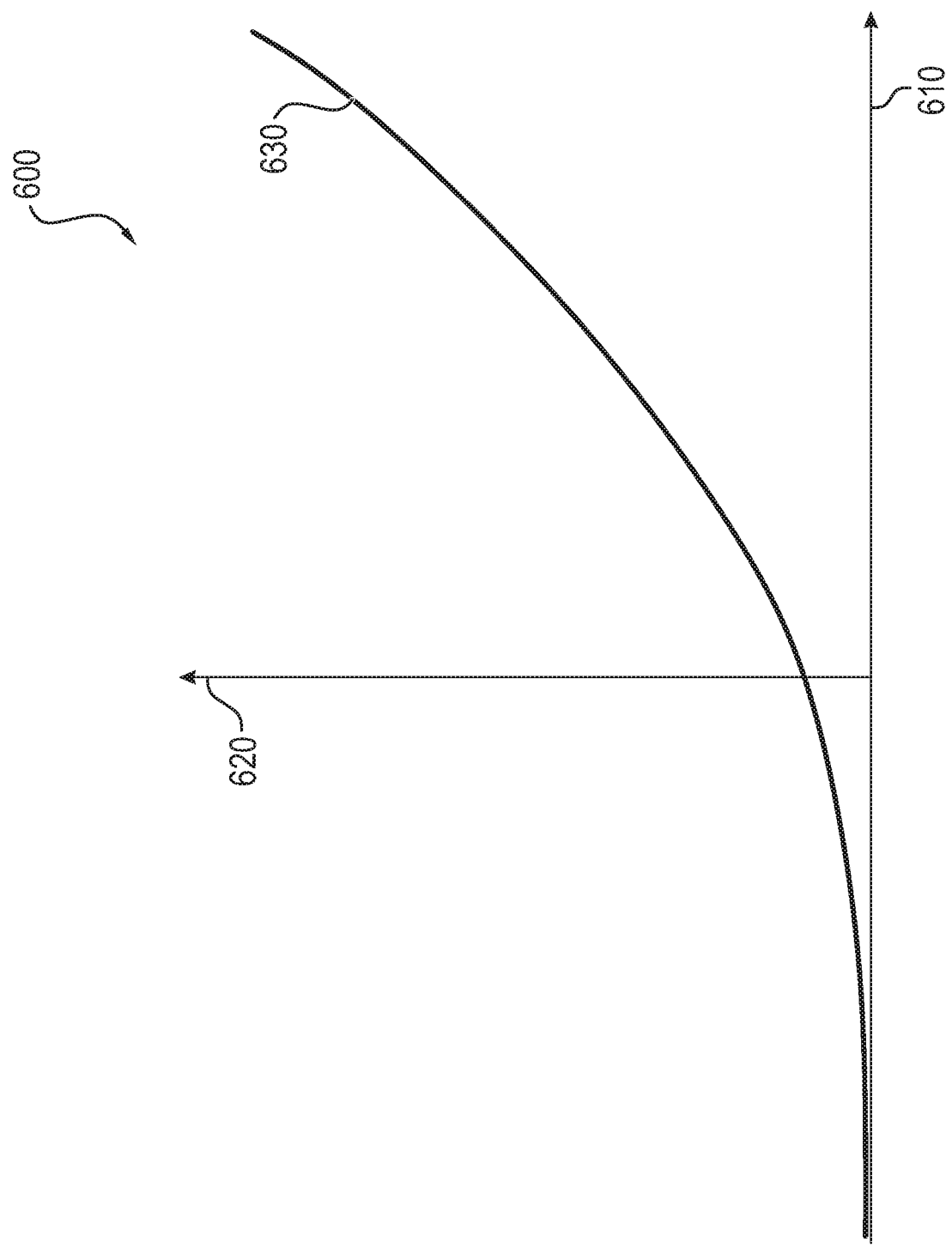
FIG. 6 is a diagram for the calculation of the current position stability value according to an exemplary embodiment of the system according to the present invention, wherein a geometric distance between a point and a plane is taken into consideration.

FIG. 5 and FIG. 6 show diagrams 500, 600 for the calculation of the current position stability value according to an exemplary embodiment of the system according to the present invention, wherein a geometric distance between two points (FIG. 5) and a geometric distance between a point of a plane (FIG. 6) are taken into account.

The two diagrams 500, 600 illustrate exemplary functions $f(D(t_x))$ for the calculation of the position stability value.

In both diagrams 500, 600, the abscissa 510, 610 shows the geometric distance D, where in the diagram 600 a negative geometric distance D means that the person's center of weight has already passed through the plane functioning as the geometric reference value.

Furthermore, the two diagrams 500, 600 show on the ordinate 520, 620 the function value f(D), which is used for the calculation of the position stability value corresponding to the exemplary calculation rules mentioned above in an advantageous exemplary embodiment.

The curve 530 of the function values of the diagram 500 clearly shows that a high position stability value can be expected if the at least one person's center of weight and the at least one geometric reference value have a short distance from one another. However, this is true only if the geometric reference value is not arranged in an edge area of the patient positioning device. A long geometric distance means in this case that the person's center of weight characterizing the person is located in an edge area of the patient positioning device, i.e., for example, in an edge area of a bed reclining surface, and therefore, there is a risk that the person will fall out of the patient positioning device. Hence, the curve 530 shows a marked lowering toward geometric distances D that are becoming longer. The curve 530 is in this case as an example not linear.

The curve 630 of the function values of the diagram 600 clearly shows that a high position stability can be expected when the distance between the person's center of weight and a geometric reference value, i.e., in the present case of a plane, is long. This is true at least if a corresponding plane is associated with a plurality of bed edges, as this is shown FIG. 3. In such a case, a long distance between the reference value and the person's center of weight means a secure position of the person in the center of the bed. The exemplary curve would, however, be different if only a reference plane is provided, so that especially long distances would again lead to a low position stability, i.e., to a falling off of the curve shape after a maximum, since such distances, just like negative distances mean that the person or at least the person's center of weight is located in the vicinity of an edge of the bed. Therefore, in the exemplary embodiment shown, the curve 630 yields a function value of almost zero for highly negative values, since the person is apparently no longer located on the patient positioning device, i.e., for example, in the bed.

As is apparent from the above description, the two diagrams 500, 600 shown are only examples. Thus, the function according to diagram 500 is used in a variant of the first exemplary embodiment of the system 100, which is shown in FIG. 1. Furthermore, the function according to diagram 600 is used in a variant of the third exemplary embodiment, which is shown in FIGS. 3 and 4.

According to the present invention, the function for analyzing the geometric distance always leads to a position stability value, which indicates a high position stability, if the person is located not at risk in the center of the patient positioning device, and a low position stability, if the person is located in edge areas of the patient positioning device and/or in a state of very high activity.

In the exemplary embodiments shown, a high position stability value also means a high indicator of position stability and therefore a low risk that the person located on the patient positioning device will fall from the patient positioning device. In exemplary embodiments, not shown, a low position stability value means a high indicator of position stability and a correspondingly large value shows a high risk that the person located on the patient positioning device will fall from the patient positioning device.

Figure 7:
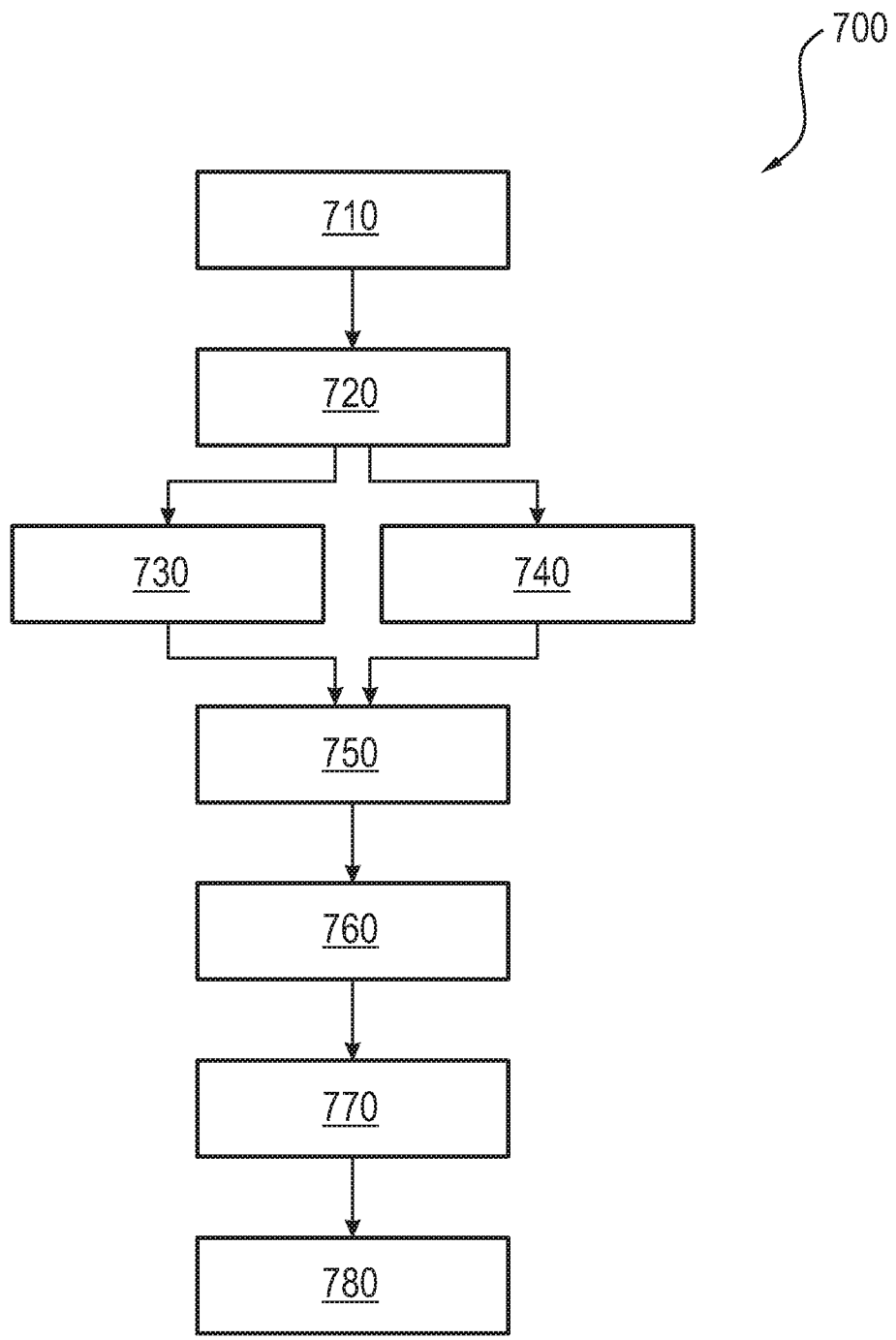
FIG. 7 is a flow chart of a first exemplary embodiment of a process according to the other aspect of the present invention.

FIG. 7 shows a flow chart of a first exemplary embodiment of the process 700 according to the other aspect of the present invention.

The process 700 according to the present invention is a process for monitoring a position stability of a person located on a patient positioning device within a monitored area in a medical setting. This process has the steps described below.

A first step 710 comprises the determination and outputting of a sensor signal in real time, wherein the sensor signal comprises sensor data, which indicate a sequence of three-dimensional views of the monitored area over a monitoring time.

A next step 720 comprises the reception of the sensor signal.

A next step 730 comprises the determination of at least one person's center of weight on the basis of the indicated three-dimensional views, wherein the at least one person's center of weight comprises information about the person located on the patient positioning device within the monitored area.

An additional step 740, which can be carried out before or after or parallel to step 730, comprises the determination of a geometric reference value on the basis of the indicated three-dimensional views, wherein the geometric reference value comprises information about the patient positioning device located within the monitored area.

A next step 750 comprises the determination of a geometric distance between the person's center of weight and the geometric reference value.

A next step 760 comprises the automated monitoring of the determined geometric distance over the course of a monitoring time in real time.

An additional step 770 comprises the calculation of a current position stability value as a function of the currently determined geometric distance and of geometric distances determined within a past analysis time interval.

A final step 780 comprises the outputting of a corresponding position stability signal.

Steps 710 and 720 are typically carried out in real time, i.e., in short consecutive time increments. Short consecutive time increments are in this case, for example, time increments of at least 0.1 sec, especially of at least 0.5 sec, e.g., time increments of 1 sec.

Steps 730 and 740 may be carried out parallel to one another or in any desired sequence following one another.

Steps 750 through 780 describe the actual monitoring operation and are carried out repeatedly in consecutive time increments, so that the respective current position stability value is always determined with a geometric distance adapted to the current situation in the monitored area.

In a preferred exemplary embodiment, the process according to the present invention comprises in a final step the outputting of an alarm generation signal if a currently calculated position stability value reaches a predefined threshold value. The alarm generation signal preferably leads to sending an alarm to another person, especially to a medical staff member.

In another step, the process according to the present invention preferably comprises the deactivation of the process 700 if the processor unit detects, due to the sensor signal, the presence of a medical staff member within the monitored area. In a preferred example of this variant, the process 700 is continued with the data detected before deactivation by the medical staff member when the detected medical staff member has left the monitored area. In a variant of this embodiment, the medical staff member is detected from among other persons by an automated detection of an identification number carried along by the medical staff member. This is possible, for example, due to a carried-along key card or a carried-along RFID chip, on which the identification number is stored, and/or due to a corresponding arrangement of an identification number on the clothing of the medical staff member. In an alternative or additional example, the identification information is provided manually by the medical staff member.

While specific embodiments of the invention have been shown and described in detail to illustrate the application of the principles of the invention, it will be understood that the invention may be embodied otherwise without departing from such principles.

LIST OF REFERENCE NUMBERS 100,200 System
104 Person positioning device (bed)
105 Patient
106 Bed mattress
107 Bedspread
108 Monitored area
109, 109' Partially monitored areas
110, 210 Sensor unit
112, 212, 212' Number of optical sensors
114 Sensor signal
120 Processor unit
121, 121', 121" Person's center of weight
122 First processing step
123, 223, 223', 223" Geometric reference value
124 Second processing step
125 Storage modulus
126 Additional processing step
127 Position stability value
129 Position stability signal
230 User interface
232 User input
234 Touch display
240 Housing
250 Alarm generation unit
252 Alarm generation signal
254 Illuminating device
360 Position securing object
500, 600 Diagram
510, 610 Abscissa
520, 620 Ordinate
530, 630 Curve
700 Process
710, 720, 730, 740, 750 Process steps
760, 770, 780
D, D', D" Geometric distance

What is claimed is:

1. A system for monitoring a position stability of a person who is located on a patient positioning device within a monitored area in a medical setting, the system comprising:
a sensor unit comprising optical sensors configured to determine a sensor signal and to output the sensor signal in real time, wherein the number of optical sensors are arranged relative to the medical setting and are configured such that the sensor signal comprises sensor data, which indicate a sequence of three-dimensional views of the monitored area over a monitoring time; and
a processor unit configured to receive the sensor signal and to determine, based on the indicated three-dimensional views, at least one person's center of weight, which comprises information about the person who is located within the monitored area on the patient positioning device, to determine, based on the indicated three-dimensional views, at least one geometric reference value that comprises information about the patient positioning device located within the monitored area, to determine a geometric distance between the at least one person's center of weight and the at least one geometric reference value, and to automatedly monitor the determined geometric distance in real time over a course of a monitoring time and to calculate a current position stability value as a function of the currently determined geometric distance and of geometric distances determined within a past analysis time interval and to output a corresponding position stability signal, wherein the current position stability value is calculated based on a rate of distance change and the rate of distance change is based on a change of the determined geometric distances.

2. A system in accordance with claim 1, further comprising an alarm generation unit configured to receive the position stability signal and to output an alarm generation signal if a currently calculated position stability value reaches a predefined threshold value.

3. A system in accordance with claim 1, wherein the person's center of weight is at least partly determined based on a predefined body weight model and based on person-specific personal data determined from the indicated three-dimensional view.

4. A system in accordance with claim 1, wherein a person's center of weight is at least partly determined based on a detection of moving regions on the patient positioning device, which moving regions are indicated by the temporal sequence of three-dimensional views.

5. A system in accordance with claim 1, wherein the processor unit is further configured to determine, based on the indicated three-dimensional views, a plurality of centers of weight of the person and to determine thereby a position pattern of the person located on the patient positioning device.

6. A system in accordance with claim 1, wherein the determined geometric reference value comprises at least one plane characterizing the patient positioning device.

7. A system in accordance with claim 1, wherein:
the current position stability value is, furthermore, dependent on an activity index determined by the processor unit; and
the activity index is based on an analysis of past three-dimensional views for the person currently located on the patient positioning device.

8. A system in accordance with claim 1, wherein:
the current position stability value is, furthermore, dependent on a position securing index determined by the processor unit; and
the position securing index is based on a detection of at least one position securing object in the three-dimensional views from a predefined group of position securing objects.

9. A system in accordance with claim 1, wherein the current position stability value is, furthermore, based on a detection by the processor unit of extremities of the person and on a current position of the extremities in relation to the person's center of weight and/or to the geometric reference value.

10. A system in accordance with claim 1, wherein the current position stability value is further based on a detection of at least one hazardous event in the three-dimensional views from a predefined group of hazardous events by the processor unit.

11. A process for monitoring the position stability of a person located on a patient positioning device within a monitored area in a medical setting, the process comprising the steps of:
- determining and outputting a sensor signal in real time, wherein the sensor signal comprises sensor data, which indicate a sequence of three-dimensional views of the monitored area over a monitoring time;
- receiving the sensor signals that have been output;
- determining at least one person's center of weight on the basis of the indicated three-dimensional views, wherein the at least one person's center of weight comprises information about the person located on the patient positioning device within the monitored area;
- determining at least one geometric reference value based on the indicated three-dimensional views, wherein the at least one geometric reference value comprises information about the patient positioning device located within the monitored area;
- determining a geometric distance between the at least one person's center of weight and the at least one geometric reference value;
- automatedly monitoring in real time the determined geometric distance in a course of a monitoring time;
- calculating a current position stability value as a function of the currently determined geometric distance and geometric distances determined within a past analysis time interval, wherein the current position stability value is calculated based on a rate of distance change and the rate of distance change is based on a change of the determined geometric distances; and outputting a corresponding position stability signal.

12. A process according to claim 11, further comprising providing a program with a program code for carrying out at least some of the steps of the process, when the program code is run on a computer, on a processor or on a programmable hardware component.

13. A process in accordance with claim 11, wherein the at least one person's center of weight is at least partly determined based on a predefined body weight model and based on person-specific personal data determined from the indicated three-dimensional view.

14. A process in accordance with claim 11, wherein the current position stability value is based on a detection of extremities of the person and on a current position of the extremities in relation to the person's center of weight and/or to the geometric reference value.

15. A process in accordance with claim 11, further comprising determining at least two other geometric reference values to provide at least three geometric reference values, each of the at least three geometric reference values comprising at least one plane characterizing the patient positioning device, wherein the currently determined geometric distance is a shortest distance between the at least one person's center of weight and the at least three geometric reference values.

16. A process in accordance with claim 15, wherein the patient positioning device is a bed and the plane characterizing the patient positioning device is a bed surface of the bed.

17. A system in accordance with claim 1, wherein the processor unit is further configured to determine at least two other geometric reference values to provide at least three geometric reference values, each of the at least three geometric reference values comprising at least one plane characterizing the patient positioning device, wherein the currently determined geometric distance is a shortest distance between the at least one person's center of weight and the at least three geometric reference values.

18. A system in accordance with claim 17, wherein the patient positioning device is a bed and the plane characterizing the patient positioning device is a bed surface of the bed.

* * * * *